United States Patent
Lehman et al.

(10) Patent No.: US 8,362,177 B1
(45) Date of Patent: Jan. 29, 2013

(54) HIGH REFRACTIVE INDEX OPHTHALMIC DEVICE MATERIALS WITH REDUCED TACK

(75) Inventors: Chance Lehman, Dallas, TX (US);
Charles Freeman, Granbury, TX (US);
Walter R. Laredo, Fort Worth, TX (US);
Ali E. Akinay, Mansfield, TX (US);
Joseph I. Weinschenk, III, Fort Worth, TX (US)

(73) Assignee: Novartis AG, Basel (CH)

( * ) Notice: Subject to any disclaimer, the term of this patent is extended or adjusted under 35 U.S.C. 154(b) by 58 days.

(21) Appl. No.: 13/100,400

(22) Filed: May 4, 2011

Related U.S. Application Data

(60) Provisional application No. 61/331,586, filed on May 5, 2010.

(51) Int. Cl.
*C08F 18/10* (2006.01)
*C08F 20/18* (2006.01)
*A61F 2/16* (2006.01)

(52) U.S. Cl. .................... 526/326; 523/106; 623/6.11

(58) Field of Classification Search .............. 526/326; 523/106; 623/6.11
See application file for complete search history.

(56) References Cited

U.S. PATENT DOCUMENTS

| | | |
|---|---|---|
| 4,304,895 A | 12/1981 | Loshaek |
| 5,290,892 A | 3/1994 | LeBoeuf et al. |
| 5,403,901 A | 4/1995 | LeBoeuf et al. |
| 5,433,746 A | 7/1995 | LeBoeuf et al. |
| 5,470,932 A | 11/1995 | Jinkerson |
| 5,603,774 A | 2/1997 | LeBoeuf et al. |
| 5,674,960 A | 10/1997 | LeBoeuf et al. |
| 5,693,095 A | 12/1997 | LeBoeuf et al. |
| 5,861,031 A | 1/1999 | LeBoeuf et al. |
| 5,939,485 A | 8/1999 | Bromberg et al. |
| 6,241,766 B1 | 6/2001 | Liao et al. |
| 6,245,106 B1 | 6/2001 | Makker et al. |
| 6,353,069 B1 | 3/2002 | Freeman et al. |
| 6,528,602 B1 | 3/2003 | Freeman et al. |
| 6,534,559 B1 | 3/2003 | Vanderlaan et al. |
| 6,534,591 B2 | 3/2003 | Rhee et al. |
| 6,544,953 B2 | 4/2003 | Tsuzuki et al. |
| 6,555,030 B1 | 4/2003 | Weinschenk, III |
| 6,635,731 B2 | 10/2003 | Mentak |
| 6,635,732 B2 | 10/2003 | Mentak |
| 6,653,422 B2 | 11/2003 | Freeman et al. |
| 6,657,029 B2 | 12/2003 | Vanderbilt |
| 6,657,030 B2 | 12/2003 | Vanderbilt |
| 6,657,032 B2 | 12/2003 | Vanderbilt |
| 6,673,886 B2 | 1/2004 | Vanderbilt |
| 6,703,466 B1 | 3/2004 | Karakelle et al. |
| 6,713,583 B2 | 3/2004 | Liao et al. |
| 6,780,899 B2 | 8/2004 | Liao et al. |
| 6,806,337 B2 | 10/2004 | Schlueter et al. |
| 6,872,793 B1 | 3/2005 | Schlueter |
| 7,037,469 B2 | 5/2006 | Hu et al. |
| 7,176,256 B2 | 2/2007 | Rhee et al. |
| 7,247,270 B2 | 7/2007 | Hu et al. |
| 7,585,900 B2 | 9/2009 | Cordova et al. |
| 7,652,076 B2 | 1/2010 | Schlueter et al. |
| 7,714,039 B2 | 5/2010 | Cordova et al. |
| 7,790,825 B2 | 9/2010 | Lehman et al. |
| 7,847,046 B2 | 12/2010 | Jinkerson et al. |
| 2006/0281888 A1 | 12/2006 | Schlueter |
| 2007/0004863 A1 | 1/2007 | Mentak |
| 2009/0088493 A1 | 4/2009 | Laredo et al. |
| 2009/0088544 A1 | 4/2009 | Laredo |
| 2009/0093603 A1 | 4/2009 | Schlueter |
| 2009/0093604 A1 | 4/2009 | Schlueter |
| 2009/0132039 A1 | 5/2009 | Cordova et al. |
| 2009/0198327 A1 | 8/2009 | Schlueter |

OTHER PUBLICATIONS www.polysciences.com, Technical Data Sheet 509, Polysciences, Inc., 2009.
www.adhesivesmag.com, Polysciences Product Sheet, Apr. 26, 2004.

*Primary Examiner* — Vu A Nguyen
(74) *Attorney, Agent, or Firm* — Patrick M. Ryan

(57) ABSTRACT

High refractive index copolymers with reduced tack are disclosed. The copolymers, which are particularly suitable for use as ophthalmic device materials, comprise a benzhydryl methacrylate or benzhydryl methacrylate derivative monomer.

21 Claims, No Drawings

HIGH REFRACTIVE INDEX OPHTHALMIC DEVICE MATERIALS WITH REDUCED TACK

CROSS-REFERENCE TO RELATED APPLICATIONS

This application claims priority under 35 U.S.C. §119 to U.S. Provisional Patent Application No. 61/331,586, filed May 5, 2010, the entire contents of which are incorporated herein by reference.

FIELD OF THE INVENTION

This invention relates to high refractive index polymers and their use in ophthalmic lenses, particularly intraocular lenses that can be inserted through small incisions.

BACKGROUND OF THE INVENTION

High refractive index acrylic materials are known for use in intraocular lenses (IOLs). For example, U.S. Pat. No. 5,290,892 discloses high refractive index acrylic materials suitable for use as IOL materials. The materials are foldable and thus capable of being inserted through small incisions. These acrylic materials contain, as principal components, two aryl acrylic monomers.

Soft acrylic materials can be tacky. It is generally desirable to reduce the amount of surface tack in materials intended for use as a foldable intraocular lens. Tacky materials can be difficult to handle and unfold. Approaches to eliminate tack include surface treatments, such as the plasma gas treatments described in U.S. Pat. No. 5,603,774. Other approaches include the use of components or additives, such as those described in U.S. Pat. Nos. 6,241,766; 6,245,106; 7,585,900; and 7,714,039.

SUMMARY OF THE INVENTION

This invention is directed to acrylic ophthalmic device materials that do not have problematic levels of tack or surface adhesion. The ophthalmic device materials are formed by copolymerizing a composition comprising
a) 50-93% of a polymerizable monomer of the structure:

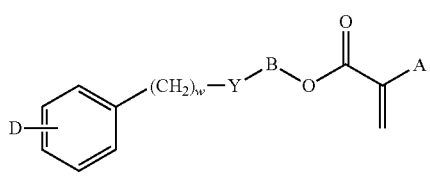

wherein: A is H or $CH_3$;
B is $(CH_2)_m$ or $[O(CH_2)_2]_z$;
m is 2-6;
z is 1-10;
Y is nothing, O, S, or NR', provided that if Y is O, S, or NR', then B is $(CH_2)_m$;
R' is H, $CH_3$, $C_{n'}H_{2n'+1}$, iso-$OC_3H_7$, $C_6H_5$, or $CH_2C_6H_5$;
n'=1-10;
w is 0-6, provided that m+w≦8; and
D is H, Cl, Br, $C_1$-$C_4$ alkyl, $C_1$-$C_4$ alkoxy, $C_6H_5$, or $CH_2C_6H_5$;

b) 5-20% of a benzhydryl methacrylate monomer of the structure

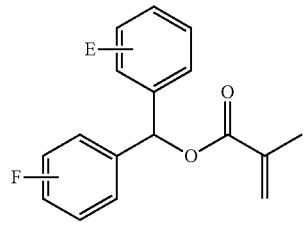

wherein: E and F are independently H, $C_1$-$C_4$ alkyl, $C_1$-$C_4$ alkoxy, $CF_3$, F, Cl, Br, or $N(CH_3)_2$; and
c) a polymerizable cross-linking agent.

These device materials can be used to form intraocular lenses with low surface tack and high refractive indexes. Lenses made of these materials are flexible and transparent, can be inserted into the eye through a relatively small incision, and recover their original shape after having been inserted.

Among other factors, the present invention is based upon the finding that the ophthalmic device materials obtained by copolymerizing the specified monomers with a cross-linking agent have relatively low surface adhesion or tack when compared to copolymeric materials containing other methacrylate components.

DETAILED DESCRIPTION OF THE INVENTION

Unless indicated otherwise, all ingredient amounts expressed in percentage terms are presented as % w/w.

The ophthalmic device materials of the present invention are formed by copolymerizing a composition comprising 50-93% of a polymerizable monomer of the structure (I):

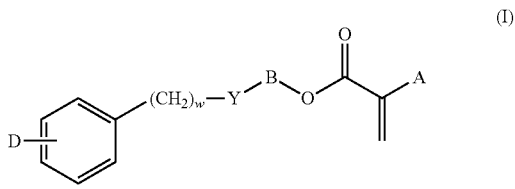

wherein: A is H or $CH_3$;
B is $(CH_2)_m$ or $[O(CH_2)_2]_z$;
m is 2-6;
z is 1-10;
Y is nothing, O, S, or NR', provided that if Y is O, S, or NR', then B is $(CH_2)_m$;
R' is H, $CH_3$, $C_{n'}H_{2n'+1}$, iso-$OC_3H_7$, $C_6H_5$, or $CH_2C_6H_5$;
n'=1-10;
w is 0-6, provided that m+w≦8; and
D is H, Cl, Br, $C_1$-$C_4$ alkyl, $C_1$-$C_4$ alkoxy, $C_6H_5$, or $CH_2C_6H_5$.

Monomers of structure (I) can be made by methods known in the art. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a base such as pyridine or triethylamine.

Suitable monomers of structure (I) include, but are not limited to: 2-ethylphenoxy acrylate; phenyl acrylate; benzyl acrylate; 2-phenylethyl acrylate; 3-phenylpropyl acrylate; 4-phenylbutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; 2-(4-propylphenyl)ethyl acrylate; 2-(4-(1-methylethyl)phenyl)ethyl acrylate; 2-(4-methoxyphenyl)ethyl acrylate; 2-(4-cyclohexylphenyl)ethyl acrylate; 2-(2-chlorophenyl)ethyl acrylate; 2-(3-chlorophenyl)ethyl acrylate; 2-(4-chlorophenyl)ethyl acrylate; 2-(4-bromophenyl)ethyl acrylate; 2-(3-phenylphenyl)ethyl acrylate; 2-(4-phenylphenyl)ethyl acrylate; 2-(4-benzylphenyl)ethyl acrylate; and their corresponding methacrylates.

Preferred monomers of formula (I) are those wherein A is H, B is $(CH_2)_m$, m is 2-5, Y is nothing or O, w is 0-1, and D is H. Most preferred are 2-phenylethyl acrylate; 4-phenylbutyl acrylate; 5-phenylpentyl acrylate; 2-benzyloxyethyl acrylate; and 3-benzyloxypropyl acrylate.

Although the total amount of the monomer of structure (I) contained in the device materials of the present invention is generally 50-93% by weight, and is preferably 75-90% by weight, of the total amount of polymerizable components of the ophthalmic device materials, such amount may comprise one monomer of structure (I) or combinations of monomers of structure (I).

In addition to the monomer(s) of structure. I, the copolymeric device materials of the present invention comprise 5-20% of a benzhydryl methacrylate monomer of structure (II):

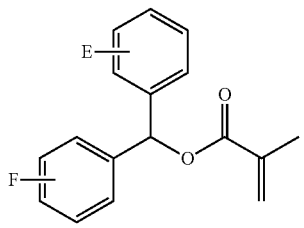

(II)

wherein: E and F are independently H, $C_1$-$C_4$ alkyl, $C_1$-$C_4$ alkoxy, $CF_3$, F, Cl, Br, or $N(CH_3)_2$; and Monomers of structure (II) are commercially available or can be made by methods known in the art. Suitable monomers of structure (II) include, but are not limited to: benzhydryl methacrylate; 4,4'-difluorobenzhydryl methacrylate; 4,4'-dimethoxybenzhydryl methacrylate; 4,4'-dichloroobenzhydryl methacrylate; 2-methylbenzhydryl methacrylate; 4-methylbenzhydryl methacrylate; 4-methoxybenzhydryl methacrylate; 4-(trifluoromethyl)benzhydryl methacrylate; 4-chlorobenzhydryl methacrylate; 2-(trifluoromethyl)benzhydryl methacrylate; 3-(trifluoromethyl)benzhydryl methacrylate; 4,4'-dimethylbenzhydryl methacrylate; 4,4'-bis(dimethylamino)benzhydryl methacrylate; 3-chloro-4'-ethylbenzhydryl methacrylate; 4-chloro-4'-ethylbenzhydryl methacrylate; 3-chloro-4'-methylbenzhydryl methacrylate; 3-chloro-4'-methoxybenzhydryl methacrylate; 3,4'-dichlorobenzhydryl methacrylate; 4-methoxy-3'-methylbenzhydryl methacrylate; 3-chloro-3'-methylbenzhydryl methacrylate; 3-chloro-3'-methoxybenzhydryl methacrylate; 4-(dimethylamino)-3'-methylbenzhydryl methacrylate; 4-(dimethylamino)-4'-methylbenzhydryl methacrylate; 4-chloro-3'-fluorobenzhydryl methacrylate; 3,3'-bis(trifluoromethyl)benzhydryl methacrylate; 3,4'-dimethylbenzhydryl methacrylate; 4-ethylbenzhydryl methacrylate; 4-tert-butylbenzhydryl methacrylate; 4-methoxy-4'-methylbenzhydryl methacrylate; 3-fluoro-3'-methylbenzhydryl methacrylate; 3-fluoro-4'-methylbenzhydryl methacrylate; 3-fluoro-4'-methoxybenzhydryl methacrylate; 4-(dimethylamino)-3'-fluorobenzhydryl methacrylate; 4-(dimethylamino)-4' fluorobenzhydryl methacrylate; 3-methoxy-3'-methylbenzhydryl methacrylate; 3-methoxy-4'-methylbenzhydryl methacrylate; 4-fluoro-4'-methoxybenzhydryl methacrylate; 4-fluoro-3'-methoxybenzhydryl methacrylate; 3-chloro-3'-fluorobenzhydryl methacrylate; 4-chloro-3'-methoxybenzhydryl methacrylate; 4-chloro-4'-methoxybenzhydryl methacrylate; 3,3'-dimethylbenzhydryl methacrylate; 4-fluorobenzhydryl methacrylate; 4-bromobenzhydryl methacrylate; 3-chloro-4'-(dimethylamino)benzhydryl methacrylate; 4-ethyl-4'-fluorobenzhydryl methacrylate; 3,3'-difluorobenzhydryl methacrylate; 4-fluoro-4'-methylbenzhydryl methacrylate; 3-chloro-4'-fluorobenzhydryl methacrylate; 3-fluoro-3'-methoxybenzhydryl methacrylate; 4-tert-butyl-4'-fluorobenzhydryl methacrylate; 4-ethyl-3'-fluoro benzhydrylmethacrylate; 3,4'-difluorobenzhydryl methacrylate; and 4-ethyl-3'-methylbenzhydryl methacrylate.

Preferred monomers of structure (II) are those wherein E and F independently are H, $CH_3$, $CF_3$, F, or Cl.

Although the total amount of the monomer of structure (II) contained in the device materials of the present invention is 5-20% by weight, is preferably 8-15% by weight, and is most preferably 10-15% by weight, of the total amount of polymerizable components of the device materials, such amount may comprise one monomer of structure (II) or combinations of monomers of structure (II).

The ophthalmic device materials of the present invention also contain a polymerizable cross-linking agent. The cross-linking agent may be any terminally ethylenically unsaturated compound having more than one unsaturated group. Suitable cross-linking agents include, for example: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; $CH_2=C(CH_3)C(=O)O-(CH_2CH_2O)_p-C(=O)C(CH_3)=CH_2$ where p=1-50; and $CH_2=C(CH_3)C(=O)O(CH_2)_tO-C(=O)C(CH_3)=CH_2$ where t=3-20; and their corresponding acrylates. A preferred cross-linking monomer is $CH_2=C(CH_3)C(=O)O-(CH_2CH_2O)_p-C(=O)C(CH_3)=CH_2$ where p is such that the number-average molecular weight is about 400, about 600, or about 1000. Other preferred cross-linking monomers are ethylene glycol dimethacrylate (EGDMA), diethylene glycol dimethacrylate, triethylene glycol dimethacrylate, triethylene glycol diacrylate, and 1,4-butanediol diacrylate (BDDA).

Generally, the total amount of the cross-linking component is at least 0.1% by weight and, depending on the identity and concentration of the remaining components and the desired physical properties, can range to about 20% by weight. The preferred concentration range for the cross-linking component is 1-5% for small, hydrophobic compounds with molecular weights typically less than 500 Daltons, and 5-17% (w/w) for larger, hydrophilic compounds with molecular weights typically between 500-5000 Daltons.

In addition to one or more monomers of structure (I), one or more monomers of structure (II), and one or more cross-linking agents, the copolymeric device materials of the present invention may also contain other ingredients, including, but not limited to, UV-absorbers, colored dyes, and hydroxyethyl methacrylate and other additives to reduce or eliminate glistenings.

An ultra-violet absorbing agent can also be included in the materials of the present invention. The ultraviolet absorbing agent can be any compound which absorbs ultraviolet light, i.e., light having a wavelength shorter than about 400 nm, but does not absorb any substantial amount of visible light. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)benzotriazoles. It is preferred to use an ultraviolet absorbing compound which is copolymerizable with the monomers and is thereby covalently bound to the polymer matrix. In this way possible leaching of the ultraviolet absorbing compound out of the lens and into the interior of the eye is minimized. Examples of suitable copolymerizable ultraviolet absorbing compounds are the substituted 2-hydroxy-benzophenones disclosed in U.S. Pat. No. 4,304,895 and the 2-hydroxy-5-acryloxyphenyl-2H-benzotriazoles disclosed in U.S. Pat. No. 4,528,311. A preferred ultraviolet absorbing compound is 2-(2'-hydroxy-3'-methallyl-5'-methyl phenyl) benzotriazole.

In addition to ultraviolet absorbing materials, ophthalmic devices made of the copolymers of the present invention may include colored dyes, such as the yellow dyes disclosed in U.S. Pat. No. 5,470,932.

The device materials of the present invention may also contain additives to reduce or eliminate glistenings. Examples of such additives include hydroxyalkyl methacrylates, such as hydroxyethyl methacrylate, and those disclosed in U.S. Published Patent Application Nos. 20090088493, 20090088544, 20090093603, and 20090093604. In one embodiment, the device materials of the present invention contain both an hydroxyalkyl methacrylate and another additive to reduce or eliminate glistenings. Preferred additives are hydroxyethyl methacrylate and those of structures (IIIa) and (IIIb).

(IIIa)

(IIIb)

where, for IIIa and IIIb, e=1-50;

X=O—, NH—, —N($CH_3$)—, —N($CH_2CH_3$)—, or —N($C_6H_5$)—;

Y=—H, —($CH_2$)$_p$OH, —$CH_2CH_2$N($CH_3$)$_2$, —$CH_2CH_2$N ($CH_2CH_3$)$_2$, —$CH_2$CH(OH)$CH_2$OH, —($CH_2$ $CH_2$O)$_q$$CH_3$, —($CH_2CH_2$O)$_q$H, —($CH_2CH_2$O)$_q$$C_6H_5$, or p=1-12;
q=1-230;
T, T' independently=O($CH_2$)$_{d'}$, NH($CH_2$)$_{d'}$, N$CH_3$($CH_2$)$_{d'}$, O($CH_2$)$_d$$C_6H_4$,
O($CH_2CH_2$O)$_d$$CH_2$, O($CH_2CH_2$O)$_d$$CH_2$, O($CH_2CH_2CH_2CH_2$O)$_d$$CH_2$, or nothing;
K=($CH_2$)$_{a'}$, O($CH_2CH_2$O)$_{b'}$, O, or nothing, provided that if T and T'=nothing, then K≠nothing;
d'=0-12;
a'=1-12;
b'=1-24;
L=H, Cl, Br, —$CH_2$C(O)$CH_3$, $CH_2$C(O)C($CH_3$)$_3$, —$CH_2$C(O)$C_6H_5$, —$CH_2$C(O)$C_6H_4$OH, —$CH_2$C(O) $C_6H_4$O$CH_3$, or —$CH_2$CH=$CH_2$;

$R^4$, $R^5$ independently =H, $CH_3$, $CH_2CH_3$, $CH_2CH_2CH_3$, CH($CH_3$)$_2$, $CH_2CH_2CH_2CH_3$, or $CH_2$CH($CH_3$)$_2$;

$R^6$=—$CO_2CH_3$, —$CO_2CH_2CH_3$, —CN, or —CONH$CH_2CH_2CH_3$; and $R^7$, $R^8$ independently =H, $CH_3$, $CH_2CH_3$, or $CH_2$OH.

The proportions of the monomers to be included in the copolymeric device materials of the present invention should be chosen so that the resulting copolymer has a glass transition temperature ($T_g$) not greater than about 37° C., which is normal human body temperature. Copolymers having glass transition temperatures higher than 37° C. are not suitable for use in foldable IOLs; such lenses could only be rolled or folded at temperatures above 37° C. and would not unroll or unfold at normal body temperature. It is preferred to use copolymers having a glass transition temperature somewhat below normal body temperature and no greater than normal room temperature, e.g., about 20-25° C., in order that IOLs made of such copolymers can be rolled or folded conveniently at room temperature. $T_g$ is measured by differential scanning calorimetry at 10° C./min., and is determined at the midpoint of the transition of the heat flux curve.

For use in IOLs, the materials of the present invention preferably exhibit sufficient strength to allow devices made of them to be folded or manipulated without fracturing. Thus, the copolymers of the present invention will have an elongation (% strain at break) of at least 100%, preferably at least 130%, and most preferably between 130 and 300%. This property indicates that lenses made of such materials generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Newton load cell. The grip distance is set at 14 mm and a crosshead speed is set at 500 mm/minute and the sample is pulled until failure. The elongation (strain) is reported as a fraction of the displacement at failure to the original grip distance. Since the materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test is begun.

The device materials of the present invention preferably have a refractive index of 1.55 to 1.56 or higher in their fully hydrated state at 35° C. For IOL applications, the stiffness of the device material must be low enough to permit folding and injection through a small diameter opening (e.g., 1-3 mm) without tearing or deforming after injection. In a preferred embodiment, the Young's Modulus of the device material will be less than 60 MPa, preferably less than 50 MPa, and most preferably between 5-40 MPa.

The copolymeric device materials preferably have an equilibrium water content of less than 1.8 weight % across the temperature range of 16-45° C. and preferably less than 1.6 weight % in the temperature range of 16-23° C. The device materials are preferably resistant to glistenings such that when equilibrated in water at 45° C. and subsequently allowed to cool to ambient temperature (approximately 22° C.) should produce very few to no microvacuoles as detected by microscopic examination.

The copolymers of this invention are prepared by conventional polymerization methods. For example, a mixture of the liquid monomers of structure (I), structure (II), and a cross-linking agent in the desired proportions, together with any other polymerizable components, such as a UV absorber, yellow dye, and/or additive to reduce or eliminate glistenings, and a conventional thermal free-radical initiator is prepared. The mixture can then be introduced into a mold of desired shape, and the polymerization carried out by heating to activate the initiator. Typical thermal free radical initiators include peroxides, such as benzoyl peroxide, peroxycarbonates, such as bis-(4-t-butylcyclohexyl)peroxydicarbonate, azonitriles, such as azobisisobutyronitrile (AIBN), and the like. A preferred initiator is AIBN. Alternatively, the monomers can be photopolymerized by using a mold which is transparent to actinic radiation of a wavelength capable of initiating polymerization. Conventional photoinitiator compounds, e.g., a benzophenone-type photoinitiator, can also be introduced to facilitate the polymerization. Regardless of the chosen initiator or curing method, the curing process should be controlled to avoid rapid polymerization, which may yield polymerized materials having more tack than the same materials polymerized more slowly.

Once the ophthalmic device materials of the present invention have been cured, they are extracted in a suitable solvent to remove as much of the unreacted components of the materials as possible. Examples of suitable solvents include acetone, methanol, and cyclohexane. A preferred solvent for extraction is acetone.

IOLs constructed of the disclosed ophthalmic device materials can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or latched, out of the material to produce the IOL.

In addition to IOLs, the ophthalmic device materials of the present invention are also suitable for use in other devices, including contact lenses, keratoprostheses, intracorneal lenses, corneal inlays or rings, and glaucoma filtration devices.

The invention will be further illustrated by the following examples which are intended to be illustrative, but not limiting.

Example 1

The formulations shown in Table 1 were prepared as follows. Components were taken from the refrigerator, freezer or cabinet and set on lab bench for about 2 hours. The components were weighed in the indicated ratios, dissolved, and vortex mixed in a 20 ml glass vial. Each formulation was purged with nitrogen for 2 minutes, placed under high vacuum (<0.5 mm Hg) for 2 minutes, injected through a 0.2 micron PTFE filter into standard polypropylene slab molds or lens wafers, and then heated: room temp. to 70° C. (20 min.), 70° C. (60 min.), 70-90° C. (60 min.), 90-105° C. (60 min.).

TABLE 1

| Formulation | PEA | BzhyMA | PMA | BDDA | Poly-PEGMA | PERK |
|---|---|---|---|---|---|---|
| A | 92.8 | 2.5 | — | 1.6 | 3.1 | 1.0 |
| B | 90.2 | 5.0 | — | 1.6 | 3.2 | 1.0 |
| C | 87.8 | 7.6 | — | 1.6 | 3.0 | 1.0 |
| D | 92.8 | — | 2.7 | 1.5 | 3.1 | 1.0 |
| E | 90.0 | — | 5.1 | 1.6 | 3.3 | 1.0 |
| F | 87.7 | — | 7.5 | 1.5 | 3.3 | 1.0 |
| G | 84.8 | 9.9 | — | 1.6 | 3.7 | 1.0 |
| H | 83.4 | 12.0 | — | 1.5 | 3.1 | 1.0 |
| I | 81.5 | 14.1 | — | 1.5 | 2.9 | 1.0 |

| | PEA | BzhyMA | PMA | BDDA | Poly-PEGMA | AIBN |
|---|---|---|---|---|---|---|
| J | 85.2 | 10.2 | — | 1.5 | 3.1 | 1.3 |
| K | 83.4 | 12.0 | — | 1.5 | 3.0 | 1.3 |
| L | 81.4 | 14.0 | — | 1.5 | 3.1 | 1.3 |

PEA: 2-phenyl methacrylate
BzhyMA: benzhydryl methacrylate
BDDA: 1,4-butanediol diacrylate
PMA: phenyl methacrylate
PolyPEGMA: methacrylate terminated macromonomer of poly(ethylene glycol) monomethyl ether methacrylate (MW = 550), Mn (SEC): 4100 Daltons, Mn (NMR): 3200 Daltons, PDI = 1.50
PERK: Perkadox 16s
AIBN: 2,2' azobisisobutyronitrile

Example 2

The mechanical properties of the copolymeric device materials of Example 1 were evaluated. Tensile bar specimens in the fashion of "dogbones" were cut from each sample group using a die and press. Typically 3 specimens per slab were prepared and 9 total specimens per formulation. Tensile properties were measured using an Instron 5543 extensometer at 500 mm/min crosshead speed. Stress at break, % strain at break, Young's modulus, the 25% secant modulus, and 100% secant modulus data were obtained. The results are shown in Table 2.

TABLE 2

| Formulation | Stress at Break (MPa) | SD (±) | Strain at Break (MPa) | SD (±) | Young's Modulus (MPa) | SD (±) | 100% Secant Modulus (MPa) | SD (±) | Modulus (Secant 25%) (MPa) | SD (±) |
|---|---|---|---|---|---|---|---|---|---|---|
| A | 2.2 | 0.4 | 132.2 | 8.8 | 4.1 | 0.3 | 1.3 | 0.0 | 1.5 | 0.0 |
| B | 2.5 | 0.2 | 140.6 | 4.7 | 5.1 | 0.3 | 1.3 | 0.0 | 1.6 | 0.0 |
| C | 2.6 | 0.2 | 144.4 | 4.8 | 6.7 | 0.5 | 1.3 | 0.0 | 1.9 | 0.1 |
| D | 1.8 | 0.2 | 134.5 | 6.7 | 3.9 | 0.2 | 1.0 | 0.0 | 1.3 | 0.0 |
| E | 2.4 | 0.3 | 141.8 | 7.1 | 5.2 | 0.3 | 1.2 | 0.0 | 1.6 | 0.0 |
| F | 2.6 | 0.3 | 147.7 | 5.5 | 7.1 | 0.3 | 1.3 | 0.0 | 2.0 | 0.0 |
| G | 3.3 | 0.5 | 146.9 | 8.7 | 9.2 | 0.5 | 1.6 | 0.0 | 2.4 | 0.1 |
| H | 4.2 | 0.4 | 158.3 | 5.3 | 14.5 | 0.5 | 1.8 | 0.0 | 3.2 | 0.1 |
| I | 4.8 | 0.5 | 157.4 | 6.9 | 21.8 | 1.2 | 2.3 | 0.1 | 4.4 | 0.2 |
| J | 3.8 | 0.4 | 163.0 | 7.5 | 10.8 | 0.8 | 1.6 | 0.0 | 2.8 | 0.1 |
| K | 4.4 | 0.6 | 162.9 | 9.5 | 14.9 | 0.7 | 2.0 | 0.0 | 3.8 | 0.1 |
| L | 5.1 | 0.5 | 162.6 | 7.7 | 21.8 | 1.6 | 2.6 | 0.1 | 5.6 | 0.2 |

Example 3

The formulations were also subjected to adhesion testing. Slabs were individually removed from the casting molds and punched to 10-mm disks using a metal die and press. One side of the disk was untouched and placed facing up in a plastic petri dish. Samples were covered with a dish cover and measured for adhesion within one hour of de-molding. The adhesion apparatus was carefully positioned and centered over the 8 mm post. A 500N load cell was used for testing. The post was positioned 1.0 mm above the hangar bottom when in the start position. The load cell was calibrated using the software calibration (Bluehill). The load cell was tarred with a 300 g weight on the hanger. A 10 mm disk was carefully positioned onto the 8 mm post and a 300 g weight placed on top of the sample. The sample plus weight were allowed to sit, untouched, for 1 minute followed by initiating the adhesion test. The hanger assembly was then pulled upward by the instrument, pulling off the sample from the 8 mm post. Max. load (N) and Energy (mJ) are shown in Table 3.

TABLE 3

| Formulation | Max load (N) | SD (±) | Energy | SD (±) |
|---|---|---|---|---|
| A | 46.4 | 7.5 | 3.4 | 0.4 |
| B | 48.9 | 3.6 | 9.6 | 2.8 |
| C | 46.1 | 5.3 | 5.1 | 1.3 |
| D | 52.8 | 5.7 | 13.8 | 0.8 |
| E | 52.7 | 5.5 | 12.4 | 3.4 |
| F | 53.2 | 5.3 | 8.5 | 3.5 |
| G | 41.3 | 5.9 | 4.2 | 0.5 |
| H | 36.4 | 4.7 | 2.2 | 0.3 |
| I | 32.9 | 2.7 | 2 | 0.2 |
| J | 37 | 7 | 3.0 | 0.5 |
| K | 27 | 2 | 2.5 | 0.2 |
| L | 24 | 3 | 2.0 | 0.3 |

Example 4

Each formulation was also tested to determine its equilibrium water content, refractive index, % extractables, and resistance to microvacuole (glistening) formation. Slabs were hydrated in a waterbath at 35° C. and the % EWC and refractive index determined. Separately, three-five polymer slabs of each cured formulation were weighed for % extractables. The polymer slabs were extracted in acetone for at least 16 hours at ambient temperature with one solvent change out after the first hour, and then allowed to dry while covered with aluminum foil at ambient temperature for 8 hours. Slabs were further dried under reduced atmosphere at 60° C. for at least 16 hours. Slabs were removed and cooled to room temperature (23° C.). Previously weighed slabs were weighed again for % extractables. Glistening resistance was determined by placing three lenses of each formulation into 20-mL vials containing ~20 mL deionized water and incubating them in a waterbath at 45° C. for 24 hours. The sample vials were removed from the water bath and placed on the lab bench to cool to room temperature (typically 23-24° C.). After cooling to room temperature, each lens was imaged using an Olympus BX60 microscope under bright field (BF) and dark field (DFA) settings at 10× with a 2× magnifier. The equilibrium water content ("EWC"), refractive index ("RI"), % extractables ("Extracts"), and glistening ("Glistenings") results are shown in Table 4.

TABLE 4

| Formulation | EWC (%) | SD (±) | RI ave | SD (±) | Extracts (%) | SD (±) | Glistenings # per locale |
|---|---|---|---|---|---|---|---|
| A | 0.72 | 0.18 | 1.5462 | 0.0006 | 1.28 | 0.04 | 0-5 |
| B | 0.84 | 0.10 | 1.5488 | 0.0004 | 1.45 | 0.16 | 0-5 |
| C | 0.68 | 0.03 | 1.5508 | 0.0003 | 1.59 | 0.14 | 0-5 |
| D | 0.81 | 0.19 | 1.5507 | 0.0003 | 1.89 | 0.24 | 0-5 |
| E | 0.76 | 0.05 | 1.5538 | 0.0013 | 1.79 | 0.14 | 0-5 |
| F | 0.77 | 0.06 | 1.5478 | 0.0008 | 1.80 | 0.13 | 0-5 |
| G | 1.15 | 0.33 | 1.5507 | 0.0018 | 1.45 | 0.06 | 0-5 |
| H | 0.90 | 0.21 | 1.5538 | 0.0013 | 1.27 | 0.07 | 0-10 |
| I | 0.64 | 0.08 | 1.5560 | 0.0000 | 1.36 | 0.09 | 0-10 |
| J | 1.12 | 0.11 | 1.5572 | 0.0003 | 2.41 | 0.10 | — |
| K | 1.13 | 0.12 | 1.5591 | 0.0004 | 2.30 | 0.09 | — |
| L | 0.93 | 0.15 | 1.5604 | 0.0011 | 2.22 | 0.13 | — |

Example 5

Sample lenses made of formulations G-I were plasma treated with Argon gas (per U.S. Pat. No. 5,603,774) and evaluated in an injection test to determine the force required to push a lens through an IOL delivery cartridge. The reported force values in Table 5 include the 10-12 N baseline force attained from pushing a plunger through an empty cartridge.

TABLE 5

| No | Force (N) | Nozzle Stress (0-5) | Temp. ° C. |
|---|---|---|---|
| Formulation G | | | |
| 1 | 24.4 | 0 | 18.4 |
| 2 | 26.0 | 0 | 18.4 |
| 3 | 20.5 | 0 | 18.4 |
| 4 | 20.4 | 0 | 18.4 |
| 5 | 26.0 | 0 | 18.4 |
| Formulation H | | | |
| 1 | 33.6 | 0 | 18.4 |
| 2 | Broken Haptic Ball | | |
| 3 | 32.9 | 0 | 18.4 |
| 4 | 32.1 | 0 | 18.4 |
| Formulation I | | | |
| 1 | 47.0 | 4 | 18.4 |
| 2 | 55.3 | 5 (Split) | 18.4 |

TABLE 5-continued

| No | Force (N) | Nozzle Stress (0-5) | Temp. ° C. |
|---|---|---|---|
| 3 | 67.0 | 5 (Split) | 18.4 |
| 4 | 56.6 | 5 (Split) | 18.4 |

Example 6

The formulation shown in Table 6a was prepared in the manner described in Example 1, except that it was cured using three different curing profiles in order to investigate the effect of the curing profile on tack. The curing conditions and tack results are shown in Table 6b. The results showed that slower heating ramp rates resulted in improved tack performance. One sample was cured with a heating ramp from room temperature to 90° C. in 15 minutes, a second sample was cured with a heating ramp from room temperature to 70° C. in 15 min., and a third was cured with a heating ramp from room temperature to 70° C. in 20 minutes. The first sample was judged to have moderate tack, whereas the second and third samples were judged to have low tack.

TABLE 6a

| Formulation | PEA | BzhyMA | TEGDMA | PolyPEGMA | AIBN |
|---|---|---|---|---|---|
| M | 84.0 | 11.5 | 1.5 | 3.0 | 1.0 |

TEGDMA: triethylene gycol dimethacrylate

TABLE 6b

| Cure Conditions of Formulation M | Max Load (N) | % Extractables |
|---|---|---|
| [1]RT to 90° C. in 15 minutes | 40 ± 4 | 6.0 ± 0.1 |
| [1]RT to 70° C. in 15 minutes | 34 ± 5 | 4.8 ± 0.1 |
| [1]RT to 90° C. in 20 minutes | 29 ± 5 | 4.8 ± 0.2 |

[1]Samples were soaked at 90° C. or 70° C. for 1 hour, then ramp heated to 110° C. in 20 minutes, and soaked at 110° C. for 2 hours.

Example 7

The formulations shown in Table 7 were prepared in the manner described in Example 1, except that the following curing profile was used: room temperature to at least 60° C. in 10-30 min. for 1 hour, then to at least 90° C. in 10-30 min. for 2 hours.

TABLE 7

| Formulation | PEA | BzhyMA | TEGDMA | TEGDA | DEGDMA | Poly PEGMA | PERK | V-65 | AIBN | TBPO | ABCC |
|---|---|---|---|---|---|---|---|---|---|---|---|
| M | 84.0 | 11.5 | 1.5 | — | — | 3.0 | — | — | 1.0 | — | — |
| N | 84.0 | 11.5 | 1.5 | — | — | 3.0 | 1.8 | — | — | — | — |
| O | 84.0 | 11.5 | 1.5 | — | — | 3.0 | — | 1.0 | — | — | — |
| P | 84.0 | 11.5 | 1.5 | — | — | 3.0 | — | — | — | 1.0 | — |
| Q | 84.0 | 11.5 | 1.5 | — | — | 3.0 | — | — | — | — | 1.0 |
| R | 84.0 | 11.5 | 2.0 | — | — | 3.0 | — | — | 1.0 | — | — |
| S | 84.0 | 11.5 | — | — | 1.5 | 3.0 | — | — | 1.0 | — | — |
| T | 84.0 | 11.5 | — | 1.5 | — | 3.0 | — | — | 1.0 | — | — |

TEGDA: triethylene gycol diacrylate
DEGDMA: diethylene glycol diamethacrylate
V-65: 2,2'-Azobis(2.4-dimethyl valeronitrile)
TBPO: Trigonox 21S (tert-butyl peroxy-2-ethylhexanoate)
ABCC: 1,1':azobis(cyclohexanecarbonitrile)

Example 8

In order to investigate the effect of the initiator on tack, formulations M, P, R, S, and T from Example 8 were tested for tack and acetone extractables using the procedures described in Examples 2-4 above. The results are shown in Table 8. Initiators with relatively higher 1 hour half-life decomposition temperatures, such as AIBN and TBPO, resulted in slower curing and better tack performance.

TABLE 8

| Formulation | Tack Load (N) | Acetone Extractables (%) |
|---|---|---|
| M | 30 ± 4 | 4.8 ± 0.1 |
| P | 26 ± 4 | 4.4 ± 0.1 |
| R | 24 ± 3 | 3.9 ± 0.1 |
| S | 28 ± 4 | 6.0 ± 0.1 |
| T | 33 ± 5 | 2.4 ± 0.1 |

Example 9

Synthesis of 4,4'-dimethoxybenzhydryl methacrylate. In a 1 L round-bottom flask equipped with magnetic stirrer and nitrogen inlet was added 700 ml anhydrous THF containing BHT as inhibitor, 98 g anhydrous pyridine, and 51.6 g (211 mmol) of 4,4'-dimethoxybenzhydrol. The reaction mixture was cooled to −10° C. and 26.5 g (254 mmol) methacryloyl chloride was added dropwise over 10 minutes. The reaction mixture was stirred at −10-0° C. for 1 hour and then stirred at ambient temperature for 20 hours. The solid was filtered and the filtrate was extracted using Et$_2$O/water. The organic layer was washed with 1 N NaHCO$_3$, 1 N HCl, brine, and water and then dried with MgSO$_4$, filtered, and concentrated under reduced pressure to give the desired crude product which was recrystallized from cold ether/hexanes at −20° C.

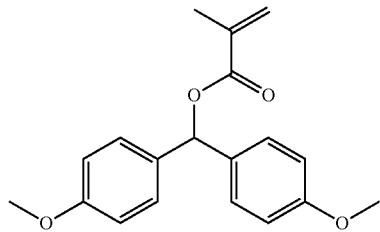

4,4'-dimethoxybenzhydryl methacrylate

Example 10

Additional formulations representative of the present invention are shown in Table 9. These formulations can be prepared by the procedure described in Example 1.

TABLE 9

| Formulation | PEA | BzhyMA | BDDA | HEMA | Poly-PEGMA | PERK |
|---|---|---|---|---|---|---|
| U | 80.2 | 5.0 | 1.6 | 10.0 | 3.2 | 1.0 |
| V | 87.8 | 7.6 | 1.6 | 5.0 | 3.0 | 1.0 |
| W | 80.0 | 9.9 | 1.6 | 4.8 | 3.7 | 1.0 |
| X | 80.4 | 12.0 | 1.5 | 3.0 | 3.1 | 1.0 |
| Y | 80.0 | 14.1 | 1.5 | 1.5 | 2.9 | 1.0 |

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. An ophthalmic device material comprising
a) 50-93% (w/w) of a polymerizable monomer of structure (I):

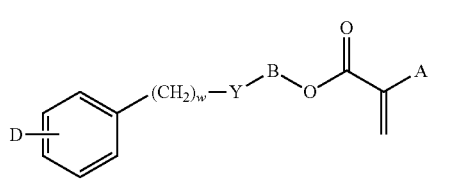

wherein: A is H or CH$_3$;
B is (CH$_2$)$_m$, or [O(CH$_2$)$_2$]$_z$;
m is 2-6;
z is 1-10;
Y is nothing, O, S, or NR', provided that if Y is O, S, or NR', then B is (CH$_2$)$_m$;
R' is H, CH$_3$, C$_n$H$_{2n'+1}$, iso-OC$_3$H$_7$, C$_6$H$_5$, or CH$_2$C$_6$H$_5$;
n'=1-10;
w is 0-6, provided that m+w≦8; and
D is H, Cl, Br, C$_1$-C$_4$ alkyl, C$_1$-C$_4$ alkoxy, C$_6$H$_5$, or CH$_2$C$_6$H$_5$;

b) 5-20% (w/w) of a benzhydryl methacrylate monomer of structure (II):

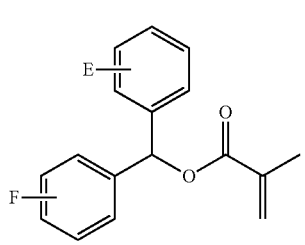

wherein: E and F are independently H, C$_1$-C$_4$ alkyl, C$_1$-C$_4$ alkoxy, CF$_3$, F, Cl, Br, or N(CH$_3$)$_2$; and
c) a polymerizable cross-linking agent.

2. The ophthalmic device material of claim 1 wherein the monomer of structure (I) is selected from the group consisting of: 2-ethylphenoxy acrylate; phenyl acrylate; benzyl acrylate; 2-phenylethyl acrylate; 3-phenylpropyl acrylate; 4-phenylbutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; 2-(4-propylphenyl)ethyl acrylate; 2-(4-(1-methylethyl)phenyl)ethyl acrylate; 2-(4-methoxyphenyl)ethyl acrylate; 2-(4-cyclohexylphenyl)ethyl acrylate; 2-(2-chlorophenyl)ethyl acrylate; 2-(3-chlorophenyl)ethyl acrylate; 2-(4-chlorophenyl)ethyl acrylate; 2-(4-bromophenyl)ethyl acrylate; 2-(3-phenylphenyl)ethyl acrylate; 2-(4-phenylphenyl)ethyl acrylate; 2-(4-benzylphenyl)ethyl acrylate; and their corresponding methacrylates.

3. The ophthalmic device material of claim 1 wherein, for the monomer of structure (I), A is H, B is (CH$_2$)$_m$, m is 2-5, Y is nothing or O, w is 0-1, and D is H.

4. The ophthalmic device material of claim 3 wherein the monomer of structure (I) is selected from the group consisting of: 2-phenylethyl acrylate; 4-phenylbutyl acrylate; 5-phenylpentyl acrylate; 2-benzyloxyethyl acrylate; and 3-benzyloxypropyl acrylate.

5. The ophthalmic device material of claim 1 wherein the ophthalmic device material comprises a total of 75-90% (w/w) of the monomer of structure (I).

6. The ophthalmic device, material of claim 1 wherein the monomer of structure (II) is selected from the group consisting of: benzhydryl methacrylate; 4,4'-difluorobenzhydryl methacrylate; 4,4'-dimethoxybenzhydryl methacrylate; 4,4'-dichloroobenzhydryl methacrylate; 2-methylbenzhydryl methacrylate; 4-methylbenzhydryl methacrylate; 4-methoxybenzhydryl methacrylate; 4-(trifluoromethyl)benzhydryl methacrylate; 4-chlorobenzhydryl methacrylate; 2-(trifluoromethyl)benzhydryl methacrylate; 3-(trifluoromethyl)benzhydryl methacrylate; 4,4'-dimethylbenzhydryl methacrylate; 4,4'-bis(dimethylamino)benzhydryl methacrylate; 3-chloro-4'-ethylbenzhydryl methacrylate; 4-chloro-4'-ethylbenzhydryl methacrylate; 3-chloro-4'-methylbenzhydryl methacrylate; 3-chloro-4'-methoxybenzhydryl methacrylate; 3,4'-dichlorobenzhydryl methacrylate; 4-methoxy-3'-methylbenzhydryl methacrylate; 3-chloro-3'-methylbenzhydryl methacrylate; 3-chloro-3'-methoxybenzhydryl methacrylate; 4-(dimethylamino)-3'-methylbenzhydryl methacrylate; 4-(dimethylamino)-4'-methylbenzhydryl methacrylate;

4-chloro-3'-fluorobenzhydryl methacrylate; 3,3'-bis(trifluoromethyl)benzhydryl methacrylate; 3,4'-dimethylbenzhydryl methacrylate; 4-ethylbenzhydryl methacrylate; 4-tert-butylbenzhydryl methacrylate; 4-methoxy-4'-methylbenzhydryl methacrylate; 3-fluoro-3'-methylbenzhydryl methacrylate; 3-fluoro-4'-methylbenzhydryl methacrylate; 3-fluoro-4'-methoxybenzhydryl methacrylate; 4-(dimethylamino)-3'-fluorobenzhydryl methacrylate; 4-(dimethylamino)-4' fluorobenzhydryl methacrylate; 3-methoxy-3'-methylbenzhydryl methacrylate; 3-methoxy-4'-methylbenzhydryl methacrylate; 4-fluoro-4'-methoxybenzhydryl methacrylate; 4-fluoro-3'-methoxybenzhydryl methacrylate; 3-chloro-3'-fluorobenzhydryl methacrylate; 4-chloro-3'-methoxybenzhydryl methacrylate; 4-chloro-4'-methoxybenzhydryl methacrylate; 3,3'-dimethylbenzhydryl methacrylate; 4-fluorobenzhydryl methacrylate; 4-bromobenzhydryl methacrylate; 3-chloro-4'-(dimethylamino) benzhydryl methacrylate; 4-ethyl-4'-fluorobenzhydryl methacrylate; 3,3'-difluorobenzhydryl methacrylate; 4-fluoro-4'-methylbenzhydryl methacrylate; 3-chloro-4'-fluorobenzhydryl methacrylate; 3-fluoro-3'-methoxybenzhydryl methacrylate; 4-tert-butyl-4'-fluorobenzhydryl methacrylate; 4-ethyl-3'-fluoro benzhydrylmethacrylate; 3,4'-difluorobenzhydryl methacrylate; and 4-ethyl-3'-methylbenzhydryl methacrylate.

7. The ophthalmic device material of claim 1 wherein, for the monomer of structure (II), E and F independently are H, $CH_3$, $CF_3$, F, or Cl.

8. The ophthalmic device material of claim 1 wherein the ophthalmic device material comprises a total of 8-15% (w/w) of the monomer of structure (II).

9. The ophthalmic device material of claim 1 wherein the cross-linking agent is selected from the group consisting of ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C(=O)O$—$(CH_2CH_2O)_p$—$C(=O)C(CH_3)$=$CH_2$ where p=1-50; and $CH_2$=$C(CH_3)C(=O)O(CH_2)_tO$—$C(=O)C(CH_3)$=$CH_2$ where t=3-20; and their corresponding acrylates.

10. The ophthalmic device material of claim 9 wherein the cross-linking agent is selected from the group consisting of: ethylene glycol dimethacrylate; diethylene glycol dimethacrylate; triethylene glycol dimethacrylate; triethylene glycol diacrylate; and 1,4-butanediol diacrylate.

11. The ophthalmic device material of claim 1 wherein the ophthalmic device material further comprises an agent selected from the group consisting of UV-absorbers; colored dyes; and additives to reduce or eliminate glistenings.

12. The ophthalmic device material of claim 11 wherein the ophthalmic device material comprises 2-(2'-hydroxy-3'-methallyl-5'-methyl phenyl)benzotriazole.

13. The ophthalmic device material of claim 11 wherein the ophthalmic device material comprises a yellow dye.

14. The ophthalmic device material of claim 11 wherein the ophthalmic device material comprises hydroxyethyl methacrylate.

15. The ophthalmic device material of claim 11 wherein the ophthalmic device material comprises an additive of structure (IIIa) or (IIIb):

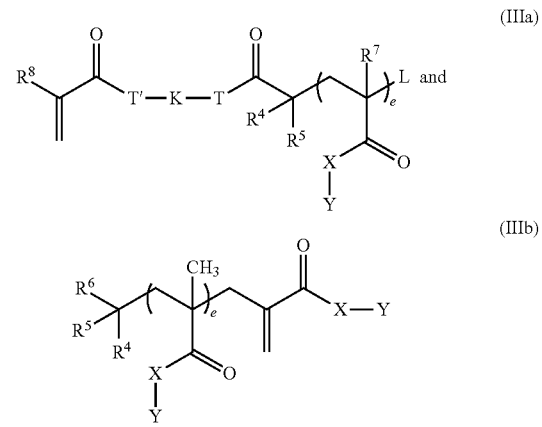

where, for IIIa and IIIb, e=1-50;

X=—O—, NH—, —N($CH_3$)—, —N($CH_2CH_3$)—, or —N($C_6H_5$)—;

Y=—H, —($CH_2$)$_p$OH, —$CH_2CH_2N(CH_3)_2$, —$CH_2CH_2N(CH_2CH_3)_2$, —$CH_2CH(OH)CH_2OH$, —($CH_2CH_2O)_q CH_3$, —($CH_2CH_2O)_q H$, —($CH_2CH_2O)_q C_6H_5$, or

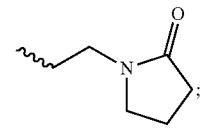

p=1-12;

q=1-230;

T, T' independently=O($CH_2$)$_{d'}$, NH($CH_2$)$_{d'}$, N$CH_3$($CH_2$)$_{d'}$, O($CH_2$)$_d C_6H_4$, O($CH_2CH_2O)_d CH_2$, O($CH_2CH_2CH_2O)_d CH_2$, O($CH_2CH_2CH_2CH_2O)_d CH_2$, or nothing;

K=($CH_2$)$_{a'}$, O($CH_2CH_2O$)$_{b'}$, O, or nothing, provided that if T and T'=nothing, then K≠nothing;

d'=0-12;

a'=1-12;

b'=1-24;

L=H, Cl, Br, —$CH_2C(O)CH_3$, $CH_2C(O)C(CH_3)_3$, —$CH_2C(O)C_6H_5$, —$CH_2C(O)C_6H_4OH$, —$CH_2C(O)C_6H_4OCH_3$,

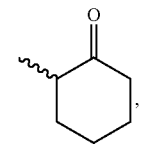

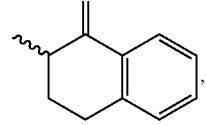

or —$CH_2CH$=$CH_2$;

$R^4$, $R^5$ independently =H, $CH_3$, $CH_2CH_3$, $CH_2CH_2CH_3$, $CH(CH_3)_2$, $CH_2CH_2CH_2CH_3$, or $CH_2CH(CH_3)_2$:

$R_6$=—$CO_2CH_3$, —$CO_2CH_2CH_3$, —CN, or —$CONHCH_2CH_2CH_2CH_3$; and $R^7$, $R^8$ independently=H, $CH_3$, $CH_2CH_3$, or $CH_2OH$.

16. The ophthalmic device material of claim 15 wherein the ophthalmic device material further comprises hydroxyethyl methacrylate.

17. The ophthalmic device material of claim 1 wherein the ophthalmic device material has a $T_g \leq 37°$ C.

18. The ophthalmic device material of claim 1 wherein the ophthalmic device material has an elongation of at least 130%.

19. The ophthalmic device material of claim 1 wherein the ophthalmic device material has a refractive index $\geq 1.55$ in a fully hydrated state at 35° C., a Young's Modulus less than 60 MPa, and an equilibrium water content of less than 1.8 weight % across the temperature range of 16-45° C.

20. An ophthalmic device comprising the ophthalmic device material of claim 1, wherein the ophthalmic device is selected from the group consisting of: intraocular lenses; contact lenses; keratoprostheses; intracorneal lenses; corneal inlays or rings; and glaucoma filtration devices.

21. An intraocular lens comprising the ophthalmic device material of claim 1.

* * * * *